(12) United States Patent
Lopez

(10) Patent No.: US 8,690,842 B2
(45) Date of Patent: Apr. 8, 2014

(54) ELECTRICAL POWER SOURCE FOR AN INTRAVENOUS FLUID HEATING SYSTEM

(75) Inventor: James T. Lopez, Dallas, TX (US)

(73) Assignee: Estill Medical Technologies, Inc., Dallas, TX (US)

( * ) Notice: Subject to any disclaimer, the term of this patent is extended or adjusted under 35 U.S.C. 154(b) by 196 days.

(21) Appl. No.: 13/227,326

(22) Filed: Sep. 7, 2011

(65) Prior Publication Data

US 2012/0078178 A1    Mar. 29, 2012

Related U.S. Application Data

(63) Continuation-in-part of application No. 12/891,463, filed on Sep. 27, 2010.

(60) Provisional application No. 61/511,466, filed on Jul. 25, 2011.

(51) Int. Cl.
*A61F 7/00* (2006.01)

(52) U.S. Cl.
USPC .......................................... 604/291; 604/113

(58) Field of Classification Search
USPC ........................................ 604/113, 114, 291
See application file for complete search history.

(56) References Cited

U.S. PATENT DOCUMENTS

| | | |
|---|---|---|
| 3,154,663 A | 10/1964 | Halvorsen |
| 3,370,153 A | 2/1968 | Fresne et al. |
| 3,443,060 A | 5/1969 | Smith |
| 3,551,641 A | 12/1970 | Truhan |
| 4,098,123 A | 7/1978 | Granzow, Jr. |
| 4,167,663 A | 9/1979 | Granzow, Jr. et al. |
| 4,231,425 A | 11/1980 | Engstrom |
| 4,314,143 A | 2/1982 | Bilstad et al. |
| 4,532,414 A | 7/1985 | Shah et al. |
| 4,559,999 A | 12/1985 | Servas et al. |
| 4,834,802 A | 5/1989 | Prier |
| 5,074,838 A | 12/1991 | Kroyer |

(Continued)

FOREIGN PATENT DOCUMENTS

| | | |
|---|---|---|
| WO | WO 87/04887 | 8/1987 |
| WO | WO00/16722 A1 | 3/2000 |

OTHER PUBLICATIONS

International Search Report dated Nov. 5, 2012 in connection with International Application No. PCT/US2012/48171.

(Continued)

*Primary Examiner* — Kevin C Sirmons
*Assistant Examiner* — Deanna K Hall

(57) ABSTRACT

An apparatus heats fluids. A number of lithium-ion cells are positioned within a housing. A first connector is positioned on a first end of the housing and operably connected to the number of lithium-ion cells. The first connector is configured to receive electrical power from a power source. A second connector is positioned on a second end of the housing and operably connected to the number of lithium-ion cells. A heating element has a tube for transferring fluid. The heating element is configured to connect to the second connector. A controller is positioned within the housing and operably connected to the number of lithium-ion cells and the second connector. The controller is configured to monitor a rate at which the electrical power is received by the heating element and limit an amount of the electrical power received by the heating element when the rate reaches a predetermined level.

20 Claims, 5 Drawing Sheets

(56) References Cited

U.S. PATENT DOCUMENTS

| | | | |
|---|---|---|---|
| 5,106,373 A | 4/1992 | Augustine et al. | |
| 5,254,094 A | 10/1993 | Starkey et al. | |
| 5,265,318 A | 11/1993 | Shero | |
| 5,269,749 A | 12/1993 | Koturov | |
| 5,325,822 A | 7/1994 | Fernandez | |
| 5,381,510 A | 1/1995 | Ford et al. | |
| 5,420,493 A * | 5/1995 | Hargadon et al. | 320/106 |
| 5,514,095 A | 5/1996 | Brightbill et al. | |
| 5,807,332 A | 9/1998 | Augustine et al. | |
| 5,875,282 A | 2/1999 | Jordan et al. | |
| 6,139,528 A | 10/2000 | Kistner et al. | |
| 6,142,974 A | 11/2000 | Kistner et al. | |
| 7,158,719 B2 | 1/2007 | Cassidy | |
| 7,377,148 B2 | 5/2008 | Cassidy et al. | |
| 7,547,295 B2 | 6/2009 | Cassidy | |
| 7,695,448 B2 | 4/2010 | Cassidy et al. | |
| 7,741,815 B2 | 6/2010 | Cassidy | |
| 7,865,072 B2 | 1/2011 | Cassidy | |
| 2001/0011585 A1 * | 8/2001 | Cassidy et al. | 165/46 |
| 2005/0008354 A1 | 1/2005 | Cassidy | |
| 2006/0210255 A1 | 9/2006 | Cassidy | |
| 2006/0222350 A1 | 10/2006 | Cassidy | |
| 2006/0291838 A1 | 12/2006 | Sturm et al. | |
| 2007/0105010 A1 * | 5/2007 | Cassidy | 429/90 |
| 2007/0126290 A1 * | 6/2007 | Jaynes et al. | 307/150 |
| 2008/0239681 A1 * | 10/2008 | Iida | 361/752 |
| 2009/0319011 A1 | 12/2009 | Rosiello | |
| 2010/0059498 A1 | 3/2010 | Hansen et al. | |
| 2010/0200506 A1 * | 8/2010 | Ware et al. | 210/647 |
| 2010/0253288 A1 | 10/2010 | Cassidy | |
| 2010/0320186 A1 * | 12/2010 | Elazari-Volcani et al. | 219/201 |
| 2011/0098642 A1 | 4/2011 | Cassidy | |
| 2011/0202034 A1 | 8/2011 | Lopez | |

OTHER PUBLICATIONS

Written Opinion of the International Search Authority in connection with International Application No. PCT/US2012/48171.

"Key Features of the Belmont buddy lite," http://www.belmontinstrument.com/products/buddylite; Belmont Instrument Corporation; Jul. 19, 2011, 1 page.

"buddy lite Fluid Warmer" Technical Specifications, http://www.belmontinstrument.com/products/buddyLiteTechSpecifications/5; Jul. 19, 2011, 2 pages.

"enFlow IV Fluid/Blood Warming System," http://vital-signs.gehealthcare.com/html/english/products/critical/enFlowFluidWarming.aspx; Vital Signs, Inc., Jul. 19, 2011, 2 pages.

Communication pursuant to Article 94(3) EPC dated Jun. 13, 2013 in connection with European Patent Application No. 11 703 357.1.

International Search Report dated Jul. 19, 2011 in connection with International Patent Application No. PCT/US2011/023889.

Written Opinion of the International Searching Authority dated Jul. 19, 2011 in connection with International Patent Application No. PCT/US2011/023889.

* cited by examiner

US 8,690,842 B2

ELECTRICAL POWER SOURCE FOR AN INTRAVENOUS FLUID HEATING SYSTEM

REFERENCE TO RELATED APPLICATION(S)

The present application is related to U.S. Provisional Patent Application No. 61/511,466, filed Jul. 25, 2011, entitled "Electrical Power Source for an Intravenous Fluid Heating System." Provisional Patent Application No. 61/511,466 is assigned to the assignee of the present application and is hereby incorporated by reference into the present application as if fully set forth herein. The present application hereby claims priority under 35 U.S.C. §119(e) to U.S. Provisional Patent Application No. 61/511,466.

The present application is also continuation-in-part application of U.S. patent application Ser. No. 12/891,463, which was filed Sep. 27, 2010 and entitled "Modular Medical Fluid Heating Apparatus." Patent application Ser. No. 12/891,463 is assigned to the assignee of the present application and is hereby incorporated by reference into the present application as if fully set forth herein. The present application hereby claims priority under 35 U.S.C. §120 to U.S. patent application Ser. No. 12/891,463.

The present application is further related to U.S. Pat. No. 6,142,974, entitled "Portable I.V. Fluid Warming System," which issued Nov. 7, 2000, and to U.S. Pat. No. 6,139,528, entitled "Intravenous Fluid Warming System," which issued Oct. 31, 2000. U.S. Pat. Nos. 6,142,974 and 6,139,528 are incorporated herein by reference into the present application as if fully set forth herein.

TECHNICAL FIELD OF THE INVENTION

The present application relates generally to portable electrical power sources and, more specifically, to a light-weight battery used in an intravenous fluid heating system.

BACKGROUND OF THE INVENTION

Intravenous (IV) fluids administered in a human body may need to have certain temperature when administrated. IV fluids, such as for example, blood, plasma, plasma extenders, Hextend™ electrolyte solution, and medications, may be refrigerated for preservation. In other examples, the IV fluids may be kept at room temperature. When administered, these IV fluids may need to be heated to avoid a chance that a patient will become hypothermic.

Medical facilities typically have electrical power and heaters for heating IV fluids to suitable body temperatures. However, outside of medical facilities it may be more difficult to obtain a power source for heating IV fluids. Additionally, medical situations that occur outside of medical facilities often need equipment that is portable and lightweight.

Therefore, there is a need in the art for an improved power source. In particular, there is a need for a power source that is portable and lightweight.

SUMMARY OF THE INVENTION

According to one advantageous embodiment of the present disclosure, an apparatus is provided for heating fluids. A number of lithium-ion cells are positioned within a housing. A first connector is positioned on a first end of the housing and is operably connected to the number of lithium-ion cells. The first connector is configured to receive electrical energy from a power source. A second connector is positioned on a second end of the housing and operably connected to the number of lithium-ion cells. A heating element has a tube for transferring fluid. The heating element is configured to connect to the second connector. A controller is positioned within the housing and operably connected to the number of lithium-ion cells and the second connector. The controller is configured to monitor a rate at which the electrical energy is received by the heating element and to limit an amount of the electrical energy received by the heating element when the rate reaches a predetermined level.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

FIGS. 1 through 8b, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged computing device.

Figure 1:
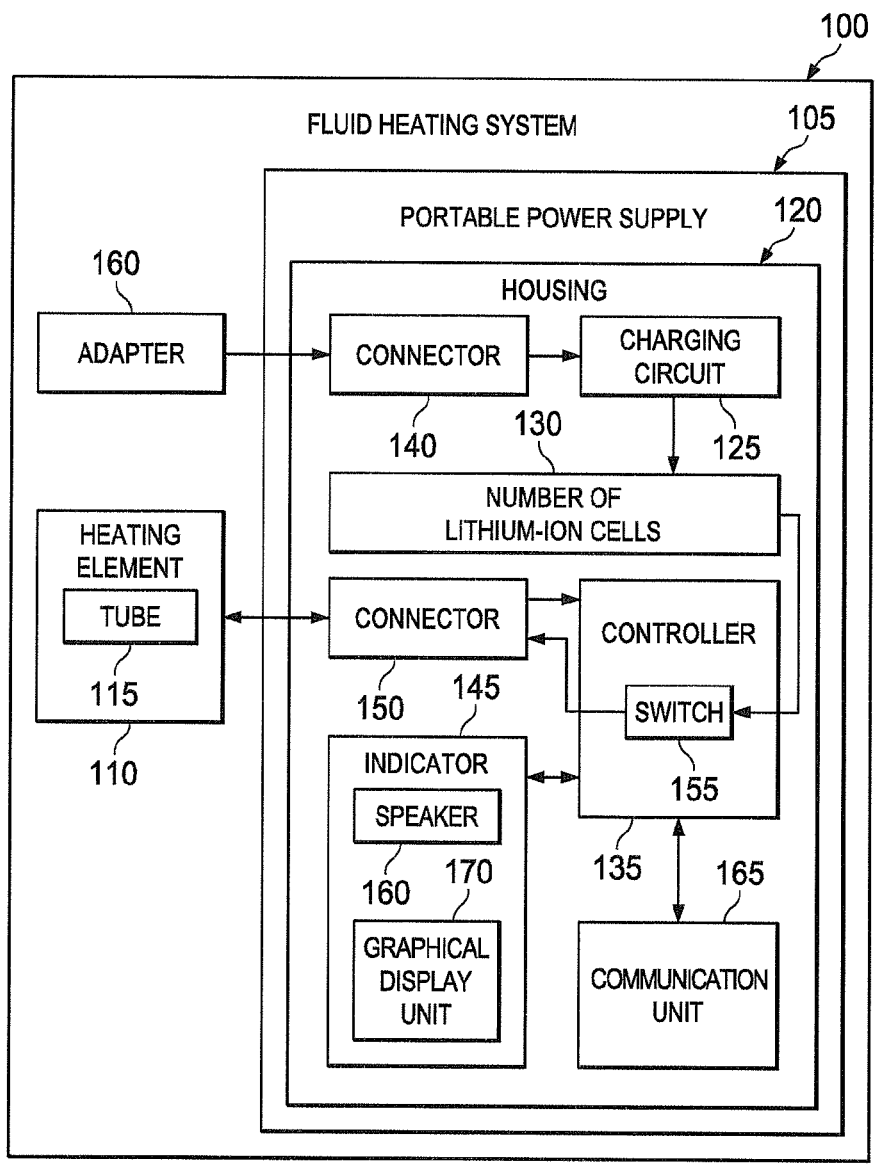
FIG. 1 illustrates a block diagram of a fluid heating system according to an advantageous embodiment of the present disclosure.

With reference now to the Figures and particularly with reference to FIG. 1, a block diagram of a fluid heating system is depicted in accordance with an advantageous embodiment of the present disclosure. Fluid heating system 100 includes portable power supply 105 and heating element 110. Portable power supply 105 is a source of electrical power that provides electrical power to heating element 110. Heating element 110 heats fluids in tube 115. For example, heating element 110 heats IV fluids prior to the fluids entering a person.

In this advantageous embodiment, portable power supply 105 is an improved battery adapted for supplying heating element 110 with electrical power for heating fluids. Portable power supply 105 includes housing 120. Housing 120 is a structure for holding components within portable power supply 105. Housing 120 contains charging circuit 125, a number of lithium-ion cells 130, and controller 135.

Charging circuit 125 is circuitry for charging the number of lithium-ion cells 130. Lithium-ion cells 130 may require a particular range of input values for voltage. For example, certain lithium-ion batteries may have a range of acceptable voltages from about 3 volts to about 4.2 volts. Voltages beyond these ranges may result in overheating of the battery or loss in life of the battery. In these examples, charging circuit 125 adapts input voltages to properly charge lithium-ion cells 130 within acceptable tolerances. For example, charging circuit 125 is adapted to receive a range of input voltages from about 10 volts of direct current (DC) to about 36 volts DC. Charging circuit 125 adapts and divides the input voltage received at connector 140 to properly charge number of lithium-ion cells 130.

Controller 135 monitors voltages in number of lithium-ion cells 130. Controller 135 displays information about the charging of number of lithium-ion cells 130 in indicator 145. For example, when number of lithium-ion cells 130 is being charged, indicator 145 may display an indication in the form of a light to indicate that number of lithium-ion cells 130 is being charged. In another example, indicator 145 includes speaker 160 that generating an audible sound indicating a status of the charge of number of lithium-ion cells 130.

Additionally, indicator 145 may display an indication of a percentage that number of lithium-ion cells 130 has been charged. For example, controller 135 identifies voltage of each cell in number of lithium-ion cells 130. Based on a known value for total charge of each cell, controller 135 illuminates a number of lights in indicator 145 that are representative of the percentage of the total charge for number of lithium-ion cells 130. For example, the lights may be light emitting diodes (LEDs) portions of a liquid crystal display (LCD), and/or any other suitable In another example, indicator 145 may generate an audible sound indicative of the percentage of the total charge for number of lithium-ion cells 130 using speaker 160. In another example, indicator 145 includes communication unit 165 for communicating a status and/or of the charge of number of lithium-ion cells 130 over a network connection using a wired, fiber, wireless and/or other suitable type of communications link. For example, communication unit 165 may be a wireless communication transceiver and/or a network interface card. Communication unit 165 may provide the charge status to an operator device or monitoring center at a remote location.

In other examples, indicator 145 includes graphical display unit 170 for displaying the charging status of number of lithium-ion cells 130. In one non-limiting example, graphical display unit 170 may be a LCD panel positioned in or on an exterior surface of housing 120. Graphical display unit 170 can also receive inputs from an operator to controller 135. For example, graphical display unit 170 may be used to turn on or off portable power supply 105 or otherwise modify and control the charging of number of lithium-ion cells 130. In some embodiments, an operator may control portable power supply 105 remotely using commands received by communication unit 165.

Controller 135 also controls the power output from portable power supply 105 at connector 150. Controller 315 includes switch 155. Switch 155 is an electrical connection between number of lithium-ion cells 130 and connector 150. Switch 155 can electrically disconnect heating element 110 from number of lithium-ion cells 130. For example, as a security feature, when controller 135 detects that number of lithium-ion cells 130 are charging, switch 155 disconnects heating element 110 from number of lithium-ion cells 130. Disconnecting heating element 110 from number of lithium-ion cells 130 reduces a chance that too much power is transferred to heating element 110 and that fluids in tube 115 will become too warm.

Additionally, controller 135 monitors a flow of current from number of lithium-ion cells 130 to heating element 110. For example, controller 135 may include a meter to monitor current flow. In these examples, to reduce a chance of overheating, heating element 110 has a threshold allowed amount of current that may be drawn from portable power supply 105. Controller 135 monitors the current flow and may limit or stop current flow to heating element 110 when the threshold is reached. In one example, controller 135 includes a fuse that prevents current flow when the threshold is reached. In another example, controller 135 includes a filter that limits the output of current at connector 150 to the threshold amount. In one illustrative example, the threshold amount of current flow for heating element 110 is about 20 amperes (amps) of current.

In some illustrative embodiments, controller 135 receives feedback information from heating element 110 through connector 150. For example, without limitation, controller 135 may receive information regarding fluid temperature, heating element performance, and historical performance data of heating element 110. Controller 135 can display the feedback information received on graphical display unit 170. In another example, controller 135 may send the feedback information to an operator or monitoring center in a remote location using communication unit 165. In these examples, an operator may use the fluid temperature information to monitor and or adjust settings of heating element 110. Additionally, historical performance data may be used to determine when tube 115 in heating element 110 should be replaced.

In this illustrative embodiment, fluid heating system 100 includes adapter 160. Adapter 160 transfers electrical power from a power source (not illustrated) to portable power supply 105 for charging number of lithium-ion cells 130. Adapter 160 connects to connector 140. In one example, adapter 160 may be an alternating current (AC) adapter for modifying an AC source into a DC input. In another example, adapter 160 is a lighter plug for charging portable power supply 105 via a lighter socket from, for example, a car or solar panel. In yet another example, adapter 160 may be a pair of electrical cables having clamps for attaching to ends of a battery. In some embodiments, adapter 160 may not be necessary. For example, the power source may connect directly to connector 140.

In this advantageous embodiment, portable power supply 105 is a portable lightweight source of power for heating element 110. In one example, portable power supply 105 has a weight of about 1.25 pounds. Portable power supply 105 supplies power for heating fluids in tube 115. In one example, heating element 110 includes a number of heating modules which are concatenated in a daisy-chain or otherwise linked or connected together. A fluid reservoir (not illustrated) such as an interventions fluid bag, is attached to the input port of the first of the series of the heating modules. An IV needle assembly is attached to the output port of a last heating module of the series of modules which are in fluid communication with each other.

In this example, fluid which moves from the reservoir through the heating modules heated by internal electrically energized coils or resistive elements located within the module that convert electrical power into thermal energy. Although internal electrically energized coils or resistive elements are described herein, any suitable heating element can be used. The temperature of the fluid is monitored as it passes through the series of modules 18. The temperature of the fluid is regulated by controller 135 by controlling the amount of current passing from number of lithium-ion cells 130 to the heating coils of the heating element 110 in response to thermal detectors located in or along the fluid path within heating element 110.

Also in this example, heating modules in heating element 110 may be concatenated or otherwise connected with other heating modules to form a longer fluid path or may be used individually. The number of heating modules in heating element 110 may be selected by the amount of heat that needs to be transferred to the fluid or a rate that the fluid travels through tube 115. By way of example, FIG. 3 and the corresponding text of U.S. patent application Ser. No. 12/891,463, incorporated by reference above, illustrate and describe a linear concatenation of heating modules that raise the temperature of a fluid in stages. FIG. 4 and the corresponding text of U.S. patent application Ser. No. 12/891,463, incorporated by reference above, illustrate and describe a 3-dimensional concatenation of heating modules that raise the temperature of a fluid in stages.

The illustration of fluid heating system 100 in FIG. 1 is not meant to imply physical or architectural limitations to the manner in which different illustrative embodiments may be implemented. Other components in addition to and/or in place of the ones illustrated may be used. Some components may be unnecessary in some illustrative embodiments. Also, the blocks are presented to illustrate some functional components. One or more of these blocks may be combined and/or divided into different blocks when implemented in different illustrative embodiments.

For example, any one of indicator 450, speaker 160, communication unit 165, and/or graphical display unit 170 may not be present in some embodiments. In other embodiments, radiofrequency identification (RFID) tags or labels may be included on portable power supply 105 for identifying portable power supply 105. In yet other embodiments, any components that may identify a position of portable power supply 105 may be disabled. For example, indicator 450, speaker 160, communication unit 165, graphical display unit 170 and/or RFID tags for portable power supply 105 may be disabled so as not to give away a position of portable power supply 105.

Figure 2:
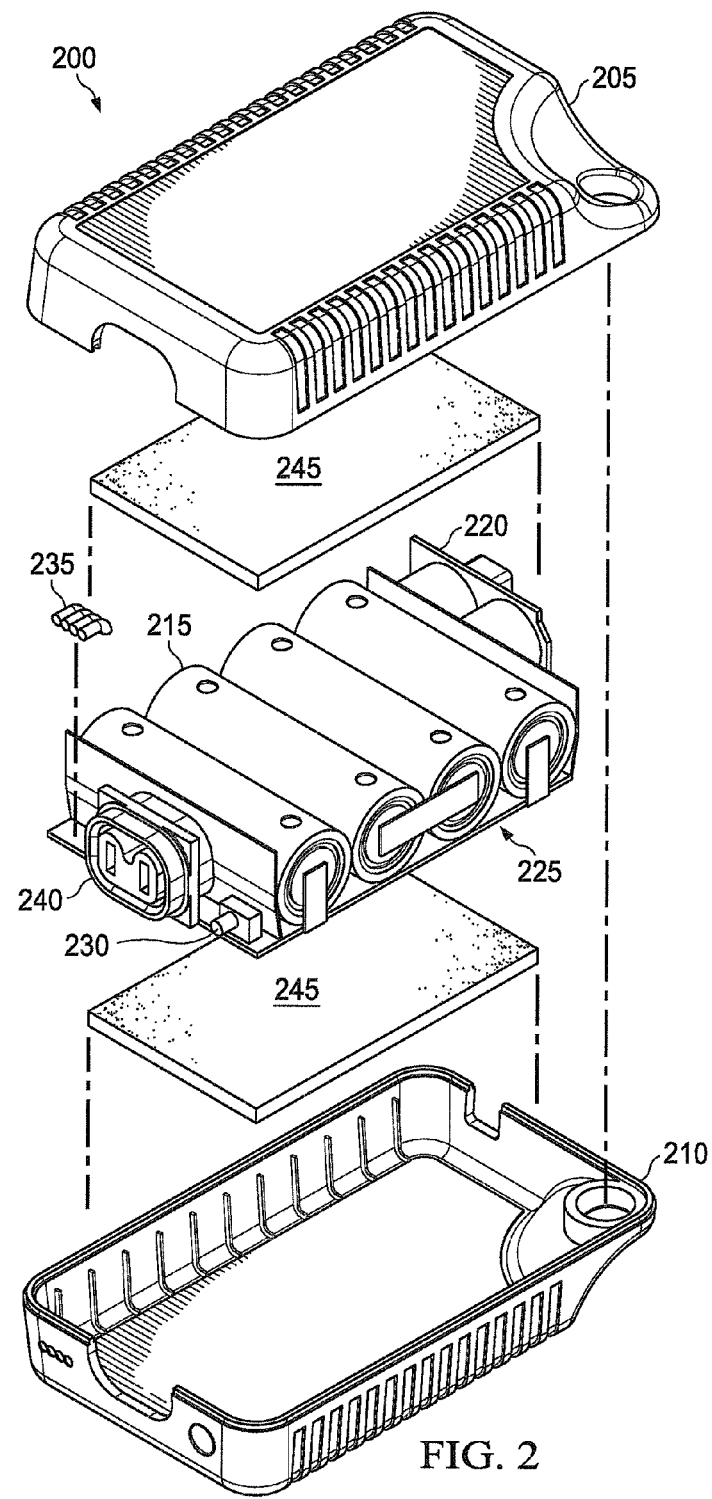
FIG. 2 illustrates an exploded view of a portable power supply according to an advantageous embodiment of the present disclosure.

FIG. 2 illustrates an exploded view of a power source according to an advantageous embodiment of the present disclosure. In this illustrative embodiment, portable power supply 200 is an example of one implementation of portable power supply 105 in FIG. 1. As illustrated, portable power supply 200 includes upper housing 205 and lower housing 210. In this illustrative example, upper housing 205 and lower housing 210 are made of a composite material, such as for example, plastic or some other type of polymer. Upper housing 205 and lower housing 210 are securely and solidly joined together it improve durability of portable power supply 200. In one example, a seam between upper housing 205 and lower housing 210 is welded using ultrasonic welding. In other examples, upper housing 205 and lower housing 210 may be mechanically or chemically joined.

Portable power supply 200 also includes lithium-ion cells 215, charging circuit 220, controller 225, indicator 230, plurality of LEDs 235, and output 240. Plurality of LEDs 235 display a percentage of charge of lithium-ion cells 215 in portable power supply 200. In this example four LEDs are illustrated; thus each light may represent about 25% of lithium-ion cells 215 being charged. In other examples, any number of LEDs may be utilized and any number of different percentages may be indicated. In this example, portable power supply 200 also includes insulating layers 245. Insulating layers 245 provide insulation against movement that may occur in portable power supply 200. In one example, insulating layers 245 are made from foam pads.

Figure 3:
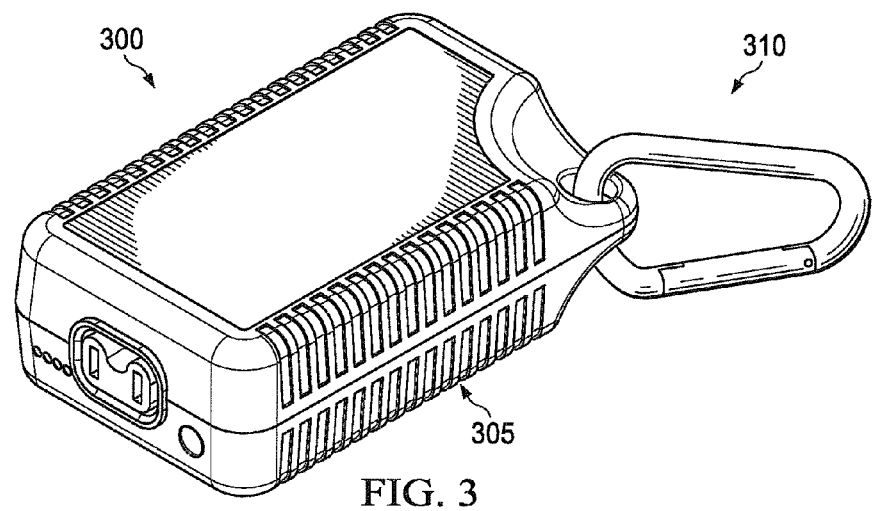
FIG. 3 illustrates a portable power supply according to an advantageous embodiment of the present disclosure.
Figure 4:
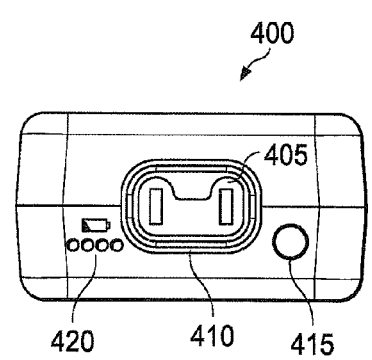
FIG. 4 illustrates a view of a side of a portable power supply according to an advantageous embodiment of the present disclosure.

FIG. 3 illustrates a portable power supply according to an advantageous embodiment of the present disclosure. Portable power supply 300 is an example of one implementation of portable power supply 200. In this depicted example, portable power supply 300 includes plurality of grooves 305 formed in the exterior surface of the housing of portable power supply 300. Plurality of grooves 305 assist operators in holding portable power supply 300. For example, plurality of grooves 305 may assist in wet or slippery conditions.

Also illustrated in this example is carabineer 310. Carabineer 310 gives an operator options in mounting and holding portable power supply 300. For example, without limitation, carabineer 310 may be utilized to secure portable power supply 300 to a stretcher, a person's clothing, a backpack, a net, a hook, or any other surface or structure in an aircraft or helicopter, or an IV fluid stand. In other examples, other types of securing devices, for example, hooks or straps, may be used in place of carabineer 310.

FIG. 4 illustrates a view of a side of a portable power supply according to an advantageous embodiment of the present disclosure. Portable power supply 400 is seen from a side view. In this illustrative example, portable power supply 400 has output 405. Output 405 is a socket type connector adapted to receive a plug type connector from a heating element, such as for example, heating element 110 in FIG. 1. Output 405 is surrounded by insulator 410. Insulator 410 reduces current flow in directions other then out of output 405. For example, portable power supply 400 may be utilized in conditions where water is preset. Insulator 410 reduces current flow into a wet environment rather than into a connected heating element.

Also illustrated are indicator 415 and plurality of LEDs 420. Indicator 415 provides an indication of whether portable power supply 400 is being charged. Plurality of LEDs 420 illustrates a percentage of charge in portable power supply 400.

Figure 5:
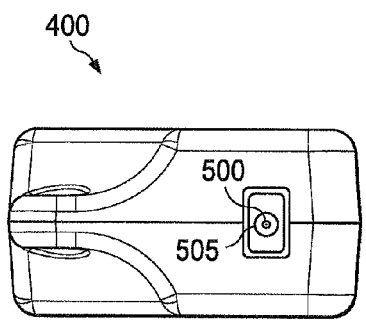
FIG. 5 illustrates a view of another side of the portable power supply in FIG. 4 according to an advantageous embodiment of the present disclosure.

FIG. 5 illustrates a view of another side of the portable power supply in FIG. 4 according to an advantageous embodiment of the present disclosure. In this illustrative example, portable power supply 400 is seen from another side. Portable power supply 400 has input 500. In this example, input 500 is a coaxial socket input, though other types of electrical connectors may be present in other embodiments. In one example, input 500 is a 2.5 mm DC input. Any number of different tips and adapters can connect to input 500 to charge portable power supply 400 via any number of different power sources. Input 500 is also surrounded by insulator 505. Insulator 505 reduces an amount of current that may leak or short from input 500.

Figure 6:
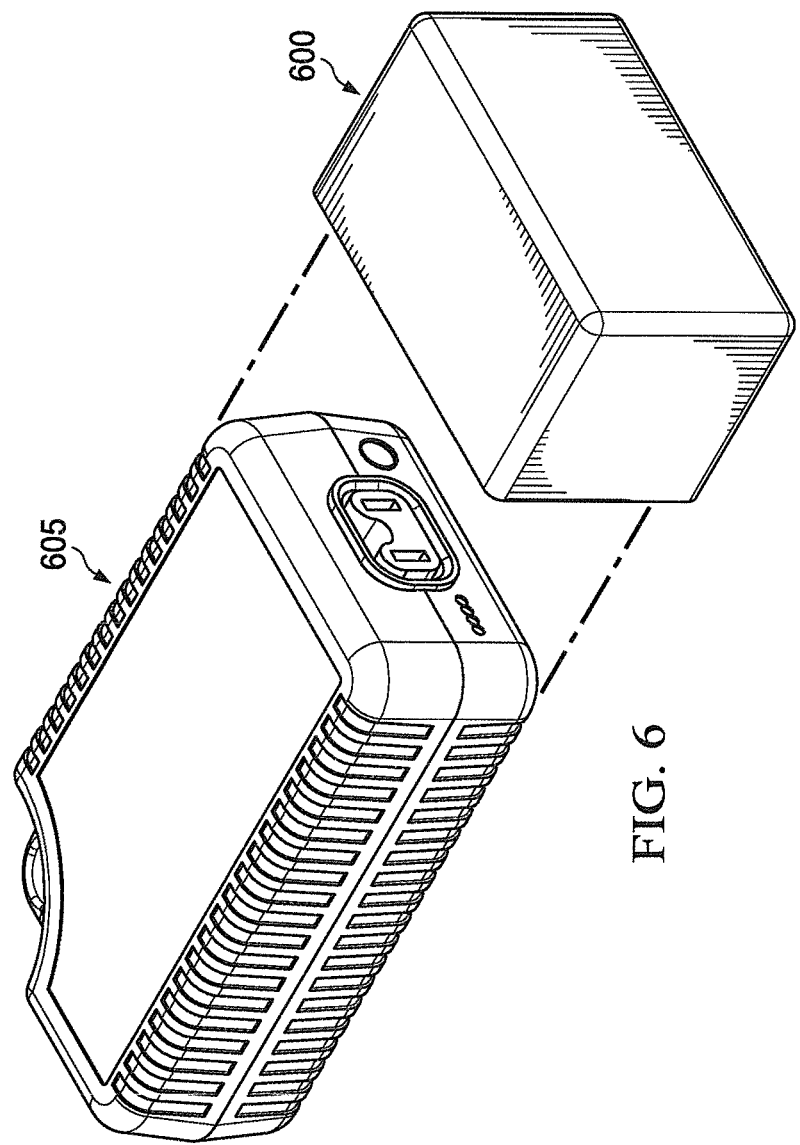
FIG. 6 is an illustration of a battery adapter module that may attach to a portable power supply according to an advantageous embodiment of the present disclosure.

FIG. 6 is an illustration of a battery adapter module that may attach to the portable power supply according to an advantageous embodiment of the present disclosure. In this illustrative example, battery adapter module 600 is configured to be attached to portable power supply 605. Portable power supply 605 is an example of one implementation of portable power supply 105. Battery adapter module 600 enables multiple devices to receive power from portable power supply 605. For example, battery adapter module 600 may include any number of different outputs for outputting power from portable power supply 605 in any number of different formats and or configurations. For example, without limitation, outputs on portable power supply 605 may include one or more of a universal serial bus (USB) connector, a lighter socket, an Institute of Electrical and Electronic Engineers (IEEE) 1394 interface (e.g. FireWire™, iLINK™, Lynx™), a Thunderbolt™ interface, Ethernet socket, an inverter with an alternating current (AC) outlet and/or any other suitable power outlet.

Figure 7:
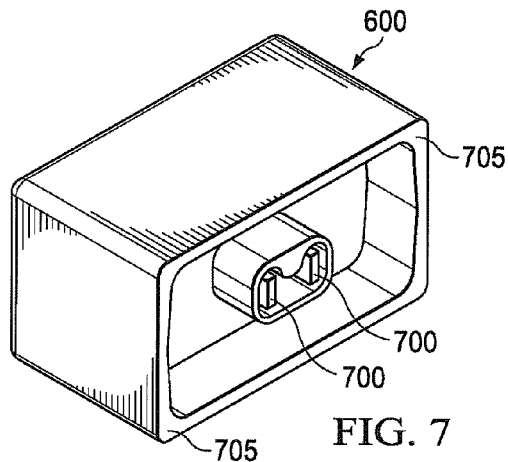
FIG. 7 is an illustration of connectors on the battery adapter module in FIG. 6 according to an advantageous embodiment of the present disclosure.

FIG. 7 is an illustration of connectors on the battery adapter module illustrated in FIG. 6. In this illustrative example, battery adapter module 600 includes connectors 700. Connectors 700 are configured to provide an electrical connection between battery adapter module 600 and portable power supply 605 in FIG. 6. In this example, connectors 700 are male pins. For example, connectors 700 from a plug that is adapted to be received by the socket of output 405 in FIG. 4. In various embodiments, battery adapter module 600 includes outer edges 705 extending from battery adapter module 600. Outer edges 705 are adapted to securely wrap around and mechanically interface with portable power supply 605 in FIG. 6. In some embodiments, outer edges 705 may be flat such that battery adapter module 600 can be connected to portable power supplies of different sizes, such as, for example, batteries described in U.S. Pat. No. 6,142,974 and U.S. Pat. No. 6,139,528. In other embodiments, an additional module (not illustrated) may be included for extending an electrical connection beyond the extension of outer edges 705 for battery adapter module 600 to be connected to portable power supplies of different sizes.

Figure 8A:
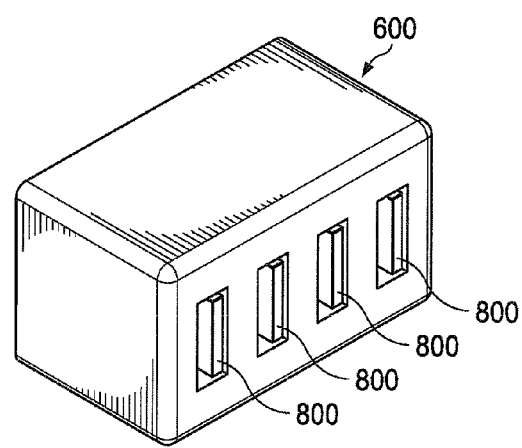
FIGS. 8a and 8b are illustrations of example configurations of the battery adapter module in FIG. 6 according to an advantageous embodiment of the present disclosure.
Figure 8B:
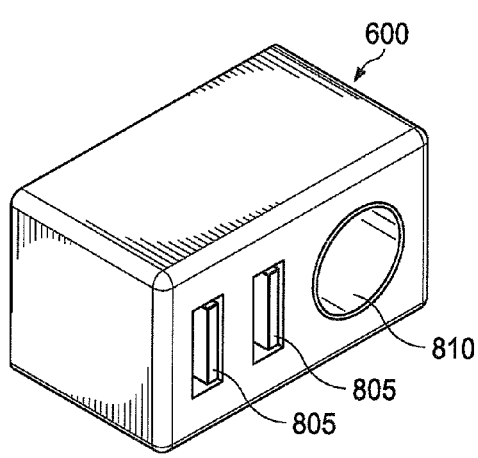

FIGS. 8*a* and 8*b* illustrate example configurations of the battery adapter module in FIG. 6. FIG. 8*a* illustrates battery adapter module 600 having four outputs. For example, the four outputs may be USB connectors 800. FIG. 8*b* illustrates battery adapter module 600 having three outputs. For example, the three outputs may include two USB connectors 805 and one lighter socket 810. The output connectors in FIGS. 8*a* and 8*b* may be used to supply power to any number of different mobile devices, such as, for example, mobile phones, tablet computers, personal digital assistants and or any other suitable mobile device. The illustration of battery adapter module 600 in FIGS. 8*a* and 8*b* are not meant to imply physical or architectural limitations to the manner in which different illustrative embodiments may be implemented. For example, any different number and type of outputs may be utilized by battery adapter module 600.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. It is intended that the present disclosure encompass such modifications and variations as fall within the scope of the appended claims.

What is claimed is:

1. An apparatus for heating fluids, the apparatus comprising:
 a number of lithium-ion cells positioned within a housing;
 a first connector positioned on a first end of the housing and operably connected to the number of lithium-ion cells, the first connector configured to receive electrical power from an external power source;
 a second connector positioned on a second end of the housing and operably connected to the number of lithium-ion cells;
 a heating element having a tube for transferring fluid, the heating element configured to connect to the second connector, receive electrical power stored in the number of lithium-ion cells, and heat the fluid by converting the electrical power into thermal energy; and
 a controller positioned within the housing and operably connected to the number of lithium-ion cells and the second connector, the controller configured to monitor a rate at which the electrical power is received by the heating element and limit an amount of the electrical power received by the heating element when the rate reaches a predetermined level, and wherein the controller is configured to electrically disconnect the second connector from the number of lithium-ion cells when the first connector is connected to the external power source.

2. The apparatus of claim 1, wherein the controller is further configured to electrically disconnect the second connector from the number of lithium-ion cells in response to the rate at which the electrical power is received by the heating element reaching the predetermined level.

3. The apparatus of claim 1 further comprising:
 a graphical display unit configured to display a charging status of the number of lithium-ion cells.

4. The apparatus of claim 3 further comprising:
 a feedback connector within the second connector, the feedback connector configured to receive feedback information from the heating element, wherein the graphical display unit is further configured to display the feedback information.

5. The apparatus of claim 3, wherein the graphical display unit is further configured to receive control inputs, and wherein the controller is further configured to control a charging state of the number of lithium-ion cells based on the control inputs received.

6. The apparatus of claim 1 further comprising:
 a communication unit configured to send information regarding a charging status of the number of lithium-ion cells to a remote location.

7. The apparatus of claim 6 further comprising:
 a feedback connector within the second connector, the feedback connector configured to receive feedback information from the heating element, wherein the communication unit is further configured to send the feedback information to a remote location.

8. The apparatus of claim 6, wherein the communication unit is further configured to receive control signals sent from the remote location in response to the information sent, and wherein the controller is further configured to control a charging state of the number of lithium-ion cells based on the control inputs received.

9. The apparatus of claim 1 further comprising:
a charging circuit connected to the number of lithium-ion cells and to the first connector, the charging circuit configured to receive a range of direct current voltage inputs to charge the number of lithium-ion cells, the range of direct current voltage inputs ranging from about ten volts to about thirty-six volts.

10. The apparatus of claim 9 further comprising:
an adapter operably connected to the charging circuit, the adapter configured to transfer an input voltage into a voltage within the range of direct current voltage inputs, wherein the adapted is one of a alternating current adapter, a pair of electrical cables, and a lighter plug.

11. The apparatus of claim 1 further comprising:
a battery adapter module configured to connect to the second connector, the battery adapter module configured to output power from the number of lithium-ion cells in a number of formats using at least one output connector.

12. The apparatus of claim 1, wherein the at least one output connector is one of a USB connector and a lighter socket.

13. The apparatus of claim 1, wherein the heating element includes a plurality of concatenated heating modules, each heating module in the plurality of concatenated heating modules comprising an input port and an output port, an input port of a first heating module of plurality of concatenated heating modules connected to a intravenous fluid supply and an output port of another heating module of plurality of concatenated heating modules connected to an intravenous fluid needle.

14. The apparatus of claim 1 further comprising:
a carabineer attached to a corner of the housing; and
a plurality of grooves in an exterior surface of the housing
wherein the housing comprises a first portion and a second portion, and wherein a seam between the first portion and a second portion is sonically welded, and
wherein a total weight of the housing is less than or equal to about two pounds.

15. A method for heating fluids, the method comprising:
storing electrical power in a number of lithium-ion cells, wherein the number of lithium-ion cells are stored in a housing and operably connected to a first connector positioned at a first end of the housing and a second connector positioned at a second end of the housing, and wherein the number of lithium-ion cells are configured to receive electrical power from an external power source via the first connector;
transferring fluid through a tube of a heating element, wherein the heating element is configured to connect with the second connector and convert electrical power into thermal energy;
receiving, by the heating element, electrical power from the number of lithium-ion cells via the second connector;
monitoring, by a controller within the housing, a rate at which the electrical power is received by the heating element and limit an amount of the electrical power received by the heating element, wherein the controller is configured to electrically disconnect the second connector from the number of lithium-ion cells when the first connector is connected to the external power source; and
transferring thermal energy from the heating element to the fluid transferring through the tube.

16. The method of claim 15, further comprising:
receiving, by the lithium-ion cells, electrical power from an external power source when the first connector is connected to the external power source;
electrically disconnecting the second connector from the number of lithium-ion cells when the first connector is connected to the external power source;
electrically disconnecting the first connector from the external power source; and
electrically connecting the second connector with the number of lithium-ion cells when the first connector is no longer connected to the external power source.

17. The method of claim 15, further comprising displaying, on a graphical display unit, a charging status of the lithium-ion cells.

18. The method of claim 15, further comprising:
receiving, by a feedback connector with the second connector, feedback information from the heating element; and
displaying, on a graphical display unit, the feedback information.

19. The method of claim 17, further comprising:
receiving, by the graphical display unit, control inputs; and
directing the controller to control a charging state of the number of lithium-ion cells based on the control inputs.

20. The method of claim 15, further comprising:
transferring electrical power to a battery adapter module connected to the second connector; and
outputting electrical power from the number of lithium-ion cells, via the battery adapter module, in a number of formats using at least one output connector.

* * * * *